United States Patent

Knoll et al.

[11] Patent Number: 5,531,118
[45] Date of Patent: Jul. 2, 1996

[54] METHOD AND DEVICE FOR OPERATING AN ULTRASONIC SENSOR

[75] Inventors: Peter Knoll, Ettlingen; Martin Noll, Muggensturm, both of Germany

[73] Assignee: Robert Bosch GmbH, Stuttgart, Germany

[21] Appl. No.: 326,453

[22] Filed: Oct. 20, 1994

[30] Foreign Application Priority Data

Nov. 12, 1993 [DE] Germany ............................ 43 38 743.8

[51] Int. Cl.⁶ .................................................. G01N 29/04
[52] U.S. Cl. ................................................ 73/628; 73/649
[58] Field of Search ............................ 73/602, 625, 628, 73/649, 597

[56] References Cited

U.S. PATENT DOCUMENTS

| | | |
|---|---|---|
| 4,210,969 | 7/1980 | Massa . |
| 4,561,064 | 12/1985 | Bruggen et al. . |
| 4,694,295 | 10/1987 | Miller et al. ............................ 340/903 |
| 4,873,676 | 10/1989 | Bailey et al. . |
| 4,903,004 | 2/1990 | Starke et al. ............................ 340/425 |
| 4,910,512 | 3/1990 | Riedel . |
| 4,910,717 | 3/1990 | Terry ........................................ 367/99 |
| 4,980,869 | 12/1990 | Forster et al. ............................ 367/99 |
| 5,334,969 | 8/1994 | Abe et al. ................................ 340/426 |
| 5,360,268 | 11/1994 | Hayashi et al. ........................... 73/602 |

FOREIGN PATENT DOCUMENTS

| | | |
|---|---|---|
| 0312849 | 4/1989 | European Pat. Off. . |
| 3420004 | 12/1985 | Germany . |
| 4120397 | 12/1992 | Germany . |
| 01250027 | 12/1989 | Japan . |
| 03238384 | 1/1992 | Japan . |
| WO85/01800 | 4/1985 | WIPO . |

Primary Examiner—Richard Chilcot
Assistant Examiner—Max H. Noori
Attorney, Agent, or Firm—Kenyon & Kenyon

[57] ABSTRACT

A method and a device for operating an ultrasonic sensor, in which the measuring sensitivity is monitored and the measuring result is compensated for temperature. This is accomplished by measuring the distance of a fixed marking, which is situated on the vehicle and has a known distance from the ultrasonic sensor, to extract a signal, whose amplitude is a measure of the sensitivity of the ultrasonic sensor. From the measured delay time and the theoretical delay time to the marking, a value is attained, which is a measure of the temperature of the ambient air. Suited as a marking is, for example, an edge of a raised license plate frame, which is mounted on a bumper bar of a motor vehicle and lies within the detecting range of the ultrasonic sensor.

12 Claims, 1 Drawing Sheet

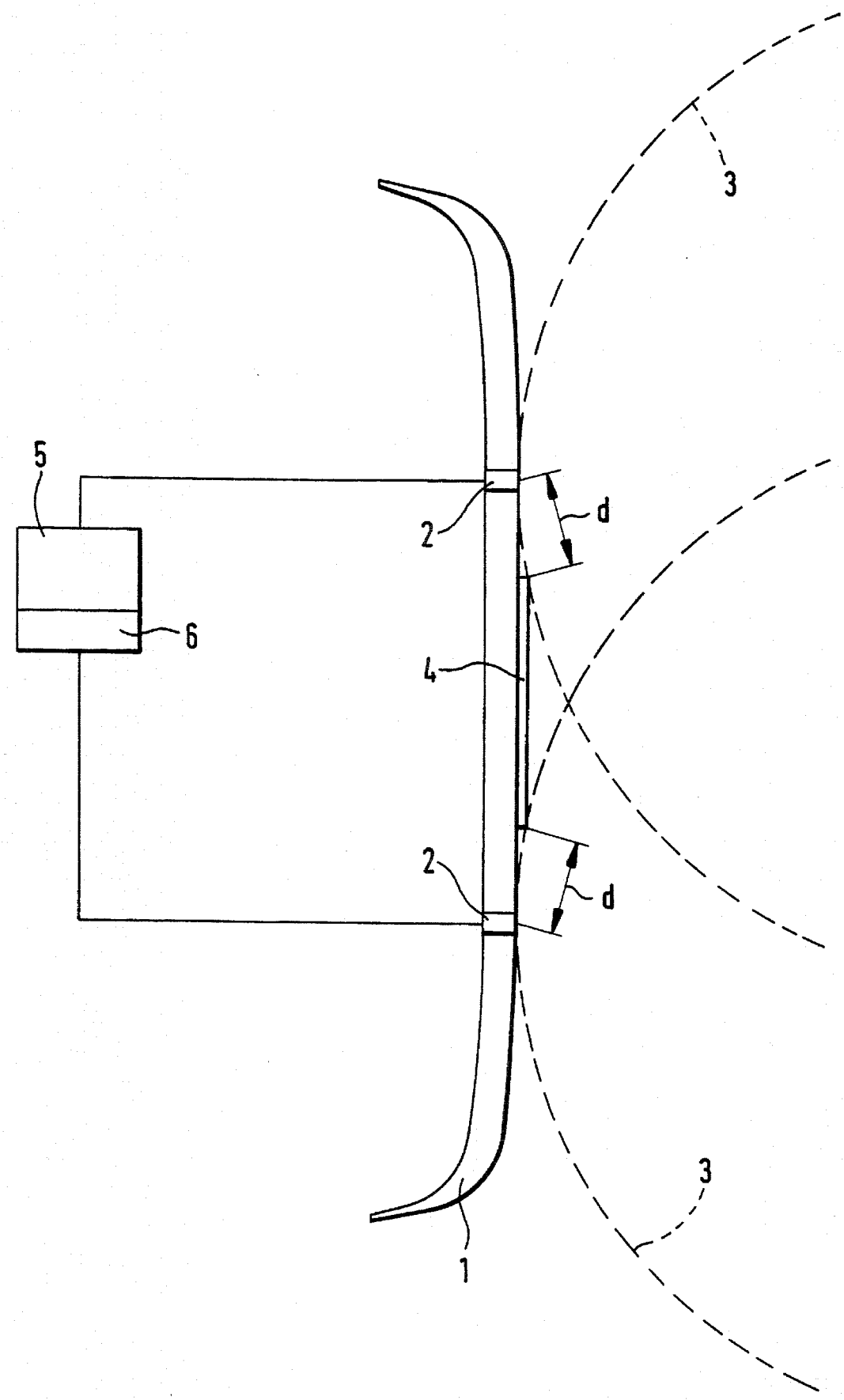

METHOD AND DEVICE FOR OPERATING AN ULTRASONIC SENSOR

FIELD OF THE INVENTION

The present invention relates to a method and device for operating an ultrasonic sensor.

BACKGROUND OF THE INVENTIONS

A distance-measuring device for motor vehicles has been described in German Patent Application No. DE 34 20 004 A1, where the delay time of ultrasonic signals is measured using two transmitting and receiving sensors, when the ultrasonic signals are reflected off of an obstacle. In this device, two methods are used to differentiate whether the reflected signal is received from the same or from another ultrasonic sensor. On the one hand, switching over from one sensor to the other is a relatively costly procedure. On the other hand, a functional control can, in fact, be carried out in this manner, but the sensitivity of the sensors is not tested. Another problem consists in that the delay time of the measured ultrasonic signal is dependent upon sound propagation in the environment. However, the speed of propagation is dependent upon temperature, so that given a changing temperature of the ambient air, one has to be prepared for a corresponding measuring error.

SUMMARY OF THE INVENTION

In contrast, an advantage of the method and device according to the present invention is that it is not only the functional reliability of an ultrasonic sensor that is tested during its operation, but the sensitivity of the ultrasonic sensor can be monitored with the aid of a specified reference mark, whose distance from the ultrasonic sensor is fixed. It is especially advantageous that the temperature of the ambient air can also be determined from the delay transmission time of the ultrasonic signal, so that from this a correction factor can be formulated, which can be used to correct the measured values of the distance to the obstacles in the vicinity of the vehicle.

It is particularly advantageous that the amplitude of the received echo signal or its relation to the transmitted signal can be used as a measure for evaluating the sensitivity of the ultrasonic sensor. The amplitude of the received echo signal or its relation to the transmitted signal can be compared to a stored value, which relates, for example, to a specific temperature, as well as to the expressly defined distance to the obstacle. Reference values of this type can either be determined empirically or be calculated on the basis of the physical interrelationships.

From the consideration of the temperature, a further advantage is attained in that the temperature value can also be displayed on the display panel of the vehicle and, thus, indicate the ambient temperature to the driver at all times. There is no need for a separate temperature sensor, which would otherwise be required to display the temperature.

In the case of an application using a plurality of ultrasonic sensors, which, for example, may be arranged symmetrically to the expressly defined reference mark, a comparison to the echo signals measured by each sensor can advantageously be made, so that the reliability of the measurement is improved in this manner.

Known ultrasonic sensors have, in part, a very wide detecting range, in which even small obstacles can be detected. If a sensor of this type is installed in a bumper of a motor vehicle, then it is even possible, for example, to detect a protruding rim (edge) of the license plate frame on the bumper bar. Since the distance between the protruding rim and the ultrasonic sensor is known, the desired values can be determined from this. The license plate frame is relatively inconspicuous, so that its rim does not interfere with the design. Thus, a simple possibility is given for controlling the ultrasonic sensor. There is no need for additional rims or markings.

One preferred application is for aiding the maneuvering of a motor vehicle in or out of a parking space, since, as a rule, during the parking operation, the measured distances are very short and, consequently, the measuring result must be very reliable to avoid a crash.

BRIEF DESCRIPTION OF THE DRAWING

The FIGURE illustrates a first exemplary embodiment according to the present invention.

DETAILED DESCRIPTION

As shown in the Figure, two ultrasonic sensors 2 are mounted on a bumper 1 of a motor vehicle, symmetrically to the middle of the vehicle. Arranged between the two sensors 2 is a license plate frame 4, whose rims are raised in relation to the bumper 1. The ultrasonic sensors 2 have a detecting range 3 shown with a dotted line, which includes a side edge of the license plate frame 4. This side edge is at a fixed distance d from the ultrasonic sensor 4 and constitutes the reference measuring distance d. In place of the license plate frame, it is, of course, possible to arrange another suited projection in the detecting range 3 of the sensor 2, to produce the measuring distance d.

The ultrasonic sensors 2 are connected to a control 5, which is known per se, for example, from German Patent Application No. DE 34 20 004 A1. The control 5 has a memory device 6, in which reference values for the distance d, the measured delay (transmission) time related to a specific temperature, and/or corresponding temperature values are filed. The arrangement of the sensors 2 is not restricted to the bumper 1, rather the sensors can also be mounted on other parts of the vehicle.

A device of this type can be used, for example, as a parking distance control for a motor vehicle. It can act as an aid for maneuvering a motor vehicle in and out of a parking space. When this device is put into operation, a control measurement can be made, there being a precise measurement made of both the amplitude of the received echo, as well as the delay time of the echo. The control 5 supplies the appropriate pulses for the sensors 2 or detects the echo received by the sensors 2. The sensitivity of the ultrasonic sensor can be exactly inferred from the amplitude of the received echo or from its relation to the transmitting signal. The control 5 compares the measured amplitude or its relation to the transmitting signal to values filed in the memory device 6. If the measured amplitude is smaller than the stored value, then the sensitivity of the sensor is lower, so that, for example, the transmitting signal or the receiving amplification can be augmented accordingly.

Given the known distance d, the delay time of the ultrasonic echo signal is dependent upon the temperature of the ambient air. For the actual ultrasonic speed c, the relation applies $$c = c_0 \cdot \sqrt{1 + \frac{\Delta T}{T_0}} \qquad (1)$$

in which case, $c_0$=331.8 m/s at the temperature $T_0$=273 K, and $\Delta T=T-T_0$. In this case, T is the momentary temperature (ambient temperature in kelvin).

Furthermore, it applies for the echo delay time that $$2d = c \cdot t \qquad (2)$$

t being equal to the echo delay time given the actual ultrasonic speed c.

By substituting equation (2) in equation (1), one obtains for the ambient temperature T $$T = \frac{4 \cdot d^2 \cdot T_0}{t^2 \cdot c_0^2} \qquad (3)$$

Thus, given the known distance d, the ambient temperature can be determined from equation (3), and this value can be shown, for example, on a display of an instrument cluster.

On the other hand, through substitution in equation (1), one obtains the actual speed of propagation c. The measurement for the distance d can then be corrected with this value according to equation (2).

The change in the ultrasonic speed c is clarified further on the basis of an example.

When T=300.3K. or $\Delta T$=27.3K., it results according to equation (1) that $$c = 331.8 \frac{m}{s} \cdot \sqrt{1 + \frac{27.3'}{273}} = 348 \frac{m}{s}$$

This correction can now be used for the additional measurements, for example, in the case of a parking operation for the vehicle, so that the measuring result is very accurate.

The advantage of outputting temperature to an appropriate display is that no additional temperature sensor is needed, which would be subjected, for example, to negative influences, such as the waste heat of the engine or of the exhaust pipe.

What is claimed is:

1. A method for operating an ultrasonic sensor arranged on a vehicle for measuring distance to an obstacle in a vicinity of the vehicle, comprising the steps of:
   controlling the ultrasonic sensor to transmit at least one ultrasonic signal and at least one ultrasonic control signal;
   evaluating an echoed ultrasonic signal received by the ultrasonic sensor, the echoed ultrasonic signal being generated as a function of the at least one ultrasonic signal and the obstacle;
   determining an ambient temperature;
   determining the measured distance to the obstacle as a function of the evaluated echoed ultrasound signal and the ambient temperature; and
   controlling a sensitivity of the ultrasonic sensor as a function of predetermined reference values and at least one of
   (a) an amplitude of an echoed ultrasound control signal, the echoed ultrasound control signal being generated as a function of the ultrasonic control signal and a reference object located a predetermined distance from the ultrasonic sensor, the reference object being in a detecting range of the ultrasonic sensor, and
   (b) a relationship of an amplitude of the ultrasonic control signal and the amplitude of the echoed ultrasonic control signal.

2. The method according to claim 1, further comprising the step of displaying the measured distance.

3. The method according to claim 1, wherein the step of determining the ambient temperature includes determining the ambient temperature as a function of the predetermined distance from the ultrasonic sensor to the reference object.

4. The method according to claim 1, wherein the step of determining the measured distance includes determining an actual speed of propagation of the ultrasonic signal as function of the ambient temperature.

5. The method according to claim 1, wherein the step of determining the ambient temperature includes determining the ambient temperature as a function of a delay time of the ultrasonic control signal to the reference object.

6. The method according to claim 5, further comprising the step of displaying the ambient temperature.

7. The method according to claim 1, wherein the step of controlling the ultrasonic sensor includes controlling at least two ultrasonic sensors, the at least two ultrasonic sensors being arranged symmetrically to the reference object, and further comprising the step of comparing the measured distance determined by each of the at least two ultrasonic sensors.

8. An ultrasonic sensing device, comprising:
   an ultrasonic sensor arranged in an area of a bumper of a vehicle for transmitting at least one ultrasonic signal and at least one ultrasonic control signal;
   a reference object arranged on the vehicle within a detecting range of the ultrasonic sensor, an echoed ultrasonic control signal being generated as a function of the ultrasonic control signal and the reference object, an echoed ultrasonic signal being generated as a function of the ultrasonic signal and an obstacle in a vicinity of the vehicle;
   a controller coupled to the ultrasonic sensor, the controller having a memory device for storing a plurality of predetermined reference values for at least one of an amplitude of an echoed ultrasonic control signal, a delay time of the echoed ultrasonic control signal, and an ambient temperature, the controller determining a sensitivity of the ultrasonic sensor as a function of the predetermined reference values and at least one of
      (a) the amplitude of the echoed ultrasound control signal, and
      (b) a relationship of an amplitude of the ultrasonic control signal and the amplitude of the echoed ultrasonic control signal.

9. The device according to claim 8, wherein the controller determines the ambient temperature as a function of the delay time of the echoed ultrasonic control signal.

10. The device according to claim 8, wherein the reference object includes one of a raised projection of the vehicle and a fixed marking on the vehicle.

11. The device according to claim 2, wherein the controller determines a distance to the obstacle to maneuver the vehicle into or out of a parking space as a function of the echoed ultrasonic signal.

12. A method for operating an ultrasonic sensor arranged on a vehicle for measuring distance to an obstacle in a vicinity of the vehicle, comprising the steps of:
   controlling the ultrasonic sensor to transmit at least one ultrasonic signal and at least one ultrasonic control signal;
   evaluating an echoed ultrasonic signal received by the ultrasonic sensor, the echoed ultrasonic signal being generated as a function of the at least one ultrasonic signal and the obstacle;

displaying the measured distance to the obstacle as a function of the evaluated echoed ultrasound signal; and controlling a sensitivity of the ultrasonic sensor as a function of predetermined reference values and at least one of
- (a) an amplitude of an echoed ultrasound control signal, the echoed ultrasound control signal being generated as a function of the ultrasonic control signal and a reference object located a predetermined distance from the ultrasonic sensor, the reference object being in a detecting range of the ultrasonic sensor, and
- (b) a relationship of an amplitude of the ultrasonic control signal and the amplitude of the echoed ultrasonic control signal.

* * * * *